United States Patent [19]

Scheuermann et al.

[11] 4,272,450
[45] Jun. 9, 1981

[54] (3-NITRO-4-METHYL)-PHENYL CHLOROFORMATE AND ITS PREPARATION

[75] Inventors: Horst Scheuermann; Dieter Schneider, both of Ludwigshafen, Fed. Rep. of Germany

[73] Assignee: BASF Aktiengesellschaft, Fed. Rep. of Germany

[21] Appl. No.: 144,059

[30] Foreign Application Priority Data

May 19, 1979 [DE] Fed. Rep. of Germany ........ 2920386

[22] Filed: Apr. 28, 1980

[51] Int. Cl.³ ............................................. C07C 69/96
[52] U.S. Cl. ................................................. 260/463
[58] Field of Search ..................................... 260/463

[56] References Cited

U.S. PATENT DOCUMENTS

| 3,715,323 | 2/1973 | Crivello | 260/463 |
| 3,742,011 | 6/1973 | Konrat et al. | 260/463 |
| 3,839,394 | 10/1974 | Konrat et al. | 260/463 |

OTHER PUBLICATIONS

N. Stamicarbon, Chem. Abstracts 68:95548a (1968), Process to Obtain Nitro Derivatives.
G. Davis et al., Chem. Abstracts 88:6463s (1978), Nitration.
Houben-Weyl, Meth. der Org. Chemie, vol. 10/1, p. 620 (1957).
Ullmans Encyklopädie der technischen Chemie, vol. 13, p. 8 (1962).

Primary Examiner—Donald G. Daus
Assistant Examiner—M. C. Eakin
Attorney, Agent, or Firm—Keil & Witherspoon

[57] ABSTRACT

The novel compound (3-nitro-4-methyl)-phenyl chloroformate is prepared by reacting (4-methyl)-phenyl chloroformate with nitric acid in the presence of sulfuric acid.

The novel compound (3-nitro-4-methyl)-phenyl chloroformate is a valuable starting material for the preparation of dyes and crop protection agents and in particular is an intermediate for the preparation of 3-nitro-4-methylphenol, which is reduced to 3-amino-4-methylphenol.

1 Claim, No Drawings

(3-NITRO-4-METHYL)-PHENYL CHLOROFORMATE AND ITS PREPARATION

The invention relates to the novel compound (3-nitro-4-methyl)-phenyl chloroformate and to a process for its preparation by reacting (4-methyl)-phenyl chloroformate with nitric acid in the presence of sulfuric acid.

It is disclosed in Houben-Weyl, Methoden der Organischen Chemie (Methods of Organic Chemistry), Volume 10/1, page 620 that methyl benzoate can be reacted with nitrating acid and sulfuric acid to give methyl 3-nitrobenzoate. It is stated, on the other hand, that benzoyl chloride, when used as the starting material, can be nitrated only without hydrolysis, using dinitrogen pentoxide in carbon tetrachloride. However, the conventional method of preparation is to convert the more readily accessible nitrated benzoic acids to the acid chloride.

We have found that (3-nitro-4-methyl)-phenyl chloroformate is obtained advantageously by reacting (4-methyl)-phenyl chloroformate with nitric acid in the presence of sulfuric acid.

Furthermore, we have found the novel compound (3-nitro-4-methyl)-phenyl chloroformate.

The reaction can be represented by the following equation:

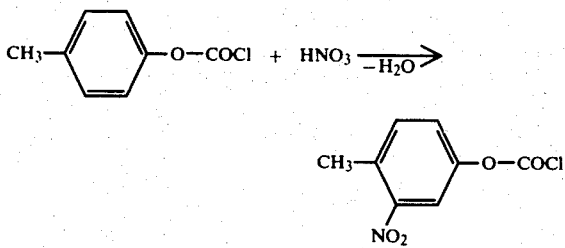

The process according to the invention gives (3-nitro-4-methyl)-phenyl chloroformate in good yield and high purity by a simple and economical method. All of these advantageous results are surprising in view of the prior art.

The nitration is carried out using nitric acid, which is advantageously concentrated or fuming nitric acid, in the presence of sulfuric acid, highly concentrated or fuming sulfuric acid advantageously being employed. All or part of the nitric acid and, if desired, the sulfuric acid can be replaced by nitrating acid, which is a mixture of the two acids. In general, nitric acid of from 85 to 100 percent strength by weight and/or sulfuric acid of from 98 to 100 percent strength by weight are used. The nitric acid is advantageously employed in a ratio of from 0.2 to 2 moles per mole of sulfuric acid in the mixture of the two acids or in the nitrating acid. As a rule, from 35 to 50, preferably from 40 to 45, percent by weight of nitric acid is used, based on (4-methyl)-phenyl chloroformate. The amount of sulfuric acid employed is preferably from 200 to 1,500, preferably from 400 to 700, percent by weight, based on (4-methyl)-phenyl chloroformate. The nitrating acid is preferably used in an amount of from 70 to 95, preferably from 75 to 85, percent by weight, based on (4-methyl)-phenyl chloroformate. In place of nitric acid it is also possible to use corresponding amounts of substances which form this acid in the reaction mixture, for example inorganic nitrates, e.g. sodium nitrate or potassium nitrate.

Urea may be used as the nitrating catalyst, advantageously in an amount of from 0.05 to 100, preferably from 5 to 10, percent by weight, based on (4-methyl)-phenyl chloroformate. The reaction is in general carried out at from $-10°$ C. to $+40°$ C., preferably from $-10°$ C. to $+25°$ C. and in particular from $0°$ C. to $5°$ C., under atmospheric or superatmospheric pressure, continuously or batchwise. The solvent medium is in general the acid or the acid mixture itself, where appropriate in the form of a mixture with water, as a correspondingly concentrated acid mixture.

The reaction can be carried out as follows: A mixture of starting material and sulfuric acid is heated to the reaction temperature and nitric acid, which may or may not be mixed with sulfuric acid, is then added slowly, for example in the course of from 15 to 30 minutes, with stirring. The mixture is kept at the reaction temperature for a further 0.5–10, preferably 0.5–1.5, hours. In a similar manner, the reaction can also be carried out continuously by, for example, feeding the above mixture, containing sulfuric acid, and the nitric acid separately into a reaction tube and thoroughly mixing the two components therein in a thin jet. Advantageously, the reaction mixture is left in the tube for from 5 to 30 minutes at the reaction temperature and is then worked up. If desired, inert gases, for example nitrogen, can be passed through the reaction chamber in order to remove nitrous gases which have formed.

The end product can then be isolated from the reaction mixture in a conventional manner, for example by precipitating on ice, which is advantageously employed in an amount of from 100 to 1,000, preferably from 200 to 300, percent by weight, based on sulfuric acid monohydrate, and filtering. Instead of isolating the pure product it is also possible to hydrolyze the crude product after renewed digestion in water at 85°–98° C. After cooling and filtering off, crude 3-nitro-4-methylphenol is obtained in a yield of over 87 percent, based on (4-methyl)-phenyl chloroformate. The product contains about 2.5 percent by weight of 2-nitro-4-methylphenol. In order to obtain pure 3-nitro-4-methylphenol, the isomer can be distilled off with steam during the hydrolysis. The moist product is advantageously hydrolyzed in boiling water in an amount of from 1.5 to 10, preferably from 3 to 4 times, that of the starting material, whilst at the same time distilling off steam and undesired 2-nitro-4-methylphenol.

The novel compound (3-nitro-4-methyl)-phenyl chloroformate is a valuable starting material for the preparation of dyes and crop protection agents and in particular is an intermediate for the preparation of 3-nitro-4-methylphenol, which is reduced to 3-amino-4-methylphenol. (Ullmanns Encyklopädie der technischen Chemie (Ullmanns Encyclopaedia of Industrial Chemistry), Volume 13, page 8). 3-amino-4-methylphenol and its derivatives are of value for the preparation of dyes.

In the Examples which follow parts are by weight.

EXAMPLE 1

(a) 85 parts of (4-methyl)-phenyl chloroformate are added slowly at from 0° to 10° C. to 340 parts of sulfuric acid monohydrate. 68 parts of mixed acid, which contains 52 parts of nitric acid and 48 parts of sulfuric acid per 100 parts, are metered in at 3° C. The mixture is stirred for a further hour and is then poured onto 1,500 parts of ice. After stirring for ½ hour, the mixture is filtered and the material on the filter is washed with ice-water until neutral. After drying, 94 parts, corresponding to 87% of theory, of (3-nitro-4-methyl)-phenyl chloroformate are obtained. The product contains 2.5 percent by weight of (2-nitro-4-methyl)-phenyl chloroformate. The pure product with a melting point of 39°–42° C. is obtained in a yield of 82.5% of theory by recrystallization from cyclohexane.

(b) The reaction is carried out by a method similar to that described in Example 1a), but after precipitating on ice and filtering off, the crude product is digested in 300 parts of water. The mixture is heated to the boil and 2-nitro-4-methyl-phenol is distilled off whilst blowing in steam. The mixture is then cooled to 25° C. and the 3-nitro-4-methylphenol which has precipitated is filtered off and dried at 40° C. (20 mbar). 65 parts of 3-nitro-4- methylphenol with a metling point of 75° C. are obtained. This corresponds to 85% of theory, based on (4-methyl)-phenyl chloroformate.

EXAMPLE 2

The reaction is carried out in a similar manner to that described in Example 1b), except that the nitration is carried out with 35 parts of 98 percent strength by weight nitric acid. The yield is 60 parts, corresponding to 78% of theory, of 3-nitro-4-methylphenol with a melting point of 72° C.

If the reaction mixture is worked up as described in Example 1a), 79.8 parts (74.1% of theory) of (2-nitro-4-methyl)-phenyl chloroformate with a melting point of 40°–42° C. are obtained.

EXAMPLE 3

85 parts of (4-methyl)-phenyl chloroformate are added slowly at from 0° to 10° C. to 400 parts of sulfuric acid monohydrate. 56 parts of potassium nitrate are introduced at 3° C. in the course of 2 hours. The mixture is stirred for a further 2 hours and is then poured onto 2,000 parts of ice to precipitate the product. After working up as described in Example 1b), 64 parts of 3-nitro-4-methylphenol with a melting point of 74° C. are obtained. This corresponds to 84% of theory, based on (4-methyl)-phenyl chloroformate.

If the reaction mixture is worked up as described in Example 1a), 81.4 parts (75.6% of theory) of (2-nitro-4-methyl)-phenyl chloroformate with a melting point of 38° to 41° C. are obtained.

EXAMPLE 4

The reaction is carried out by a method similar to that described in Example 1b), but using 575 parts of sulfuric acid (98% by weight) in place of the sulfuric acid monohydrate. 48.8 parts of 3-nitro-4-methylphenol with a melting point of 75° C. are obtained. This corresponds to 64% of theory, based on (4-methyl)-phenyl chloroformate.

If the reaction mixture is worked up as described in Example (1a), 62 parts (57.6% of theory) of (2-nitro-4-methyl)-phenyl chloroformate with a melting point of 40° to 42° C. are obtained.

EXAMPLE 5

The reaction is carried out in a similar manner to that described in Example 1a), but after the nitration working up is carried out by adding the reaction mixture to 1,500 parts of water and subjecting the resulting mixture to a steam distillation, during which the crude (3-nitro-4-methyl)-phenyl chloroformate is hydrolyzed and 2-nitro-4-methyl-phenol is distilled off at the same time. The mixture is cooled to 25° C. and the 3-nitro-4-methylphenol which has precipitated is filtered off and dried at 40° C. (20 mbar). 68 parts of 3-nitro-4-methylphenol with a melting point of 73°–76° C. are obtained. This corresponds to 89% of theory, based on (4-methyl)-phenyl chloroformate.

We claim:

1. (3-Nitro-4-methyl)-phenyl chloroformate.

* * * * *